United States Patent [19]

Harper

[11] 4,425,912

[45] Jan. 17, 1984

[54] KNEE PROTECTOR/STABILIZER

[75] Inventor: Oris E. Harper, Asheboro, N.C.

[73] Assignee: Rampon Products, Inc., Asheboro, N.C.

[21] Appl. No.: 387,757

[22] Filed: Jun. 11, 1982

[51] Int. Cl.³ .............................................. A61F 3/00
[52] U.S. Cl. ...................................... 128/80 C; 2/24
[58] Field of Search ................... 128/80 C, 165, 87 R; 2/22, 24

[56] References Cited

U.S. PATENT DOCUMENTS 3,046,981  7/1962  Biggs, Jr. et al. ................. 128/80 C
4,116,236  9/1978  Albert ............................... 128/80 C
4,201,203  5/1980  Applegate ......................... 128/80 C
4,296,744 10/1981  Palumbo ........................... 128/80 C
4,353,362 10/1982  De Marco ......................... 128/80 C Primary Examiner—John D. Yasko
Attorney, Agent, or Firm—B. B. Olive

[57] ABSTRACT

A knee protector/stabilizer is formed from tubular knit stretch material with stays attached to the exterior sides thereof and which has an internal covered pad arrangement attached at selected points on the inside of the protector/stabilizer in the area of the knee and at other selected points attached to straps which are adjustable from the outside of the protector/stabilizer.

4 Claims, 6 Drawing Figures

KNEE PROTECTOR/STABILIZER

DESCRIPTION

1. Technical Field

The present invention relates to devices developed for wear by individuals and particularly sports participants to protect from injury or the exaggeration of existing physical ailments. Specifically, the present invention relates to devices received by the leg of the wearer and which are positioned over the knee for protecting or stabilizing the knee joint.

2. Background Art

A frequently employed approach to protect and provide strength to the knee area has been to apply adhesive tape around the joint. Going beyond this approach, stretch bandages, braces, guards, and the like, are now available to the individual.

U.S. Pat. Nos. 1,092,836; 2,311,483; 3,194,233; 3,387,305; 3,533,106; 3,786,804 and 3,945,046 are illustrative of an evolution of devices along the lines of the present invention.

However, even though there is a wide variety in the types of devices available, applicant is unaware of a circular knit knee brace which acts as both a knee protector and knee stabilizer and which has spiral stays attached to the side and internal pads for padding the kneecap area and which are adjustable externally of the brace.

DISCLOSURE OF THE INVENTION

In accordance with the present invention, applicant provides a knee protector/stabilizer formed of a circular rib knit elastic fabric with vertical spiral stays attached to the outside of the brace. Within the brace, a pair of pads are enclosed in fabric pouches which are attached at selected points inside the brace. Additionally, the pouches containing the pads are attached to straps which pass through the brace and are arranged so that they can be adjusted outside the brace to adjust the internal position of the pads on the knee.

BEST MODE FOR CARRYING OUT THE INVENTION

Figure 1:
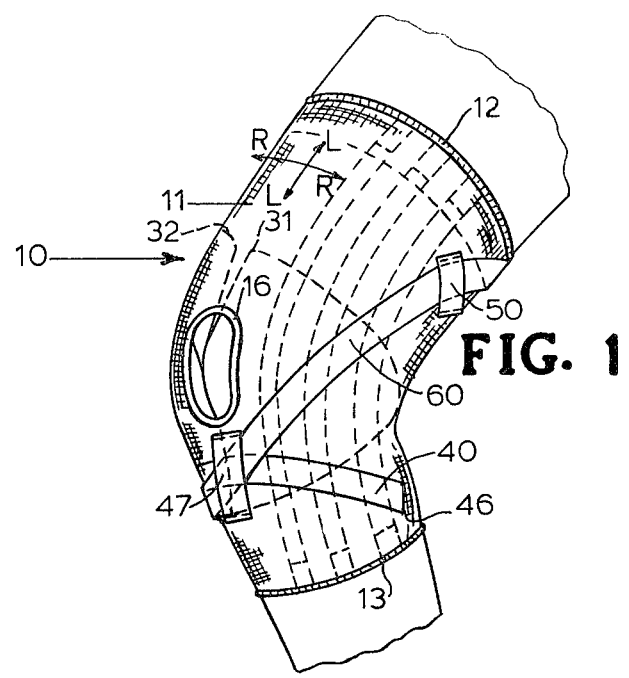
FIG. 1 is a pictorial view of the knee protector/stabilizer or brace of the invention showing the same in use on the leg of an individual.
Figure 2:
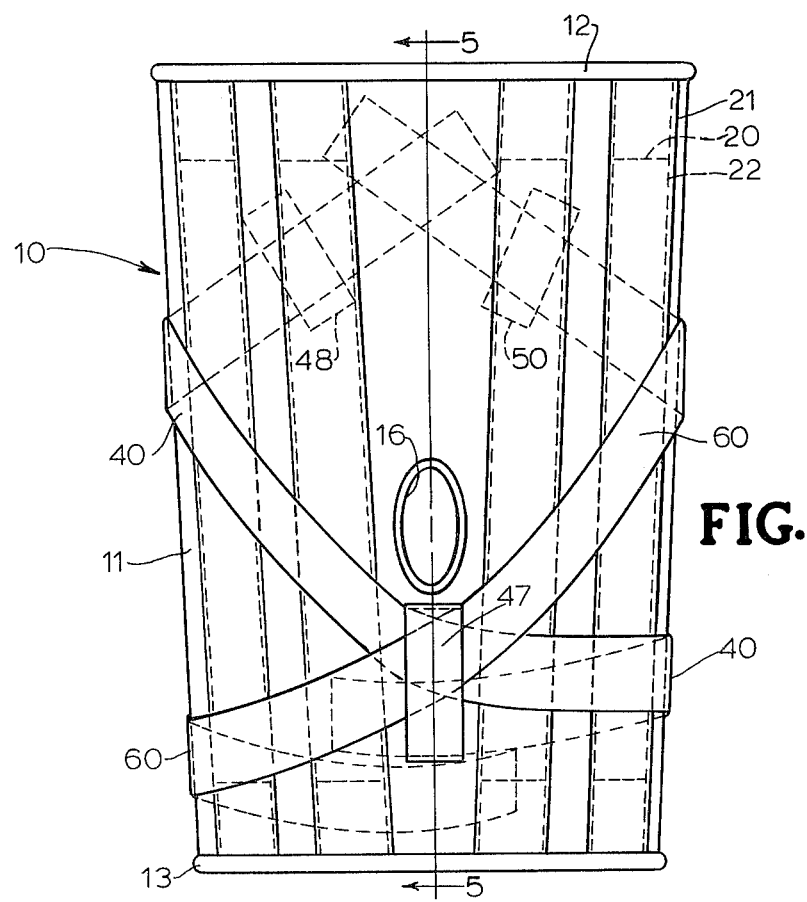
FIG. 2 is a front view of the protector/stabilizer of the invention.
Figure 5:
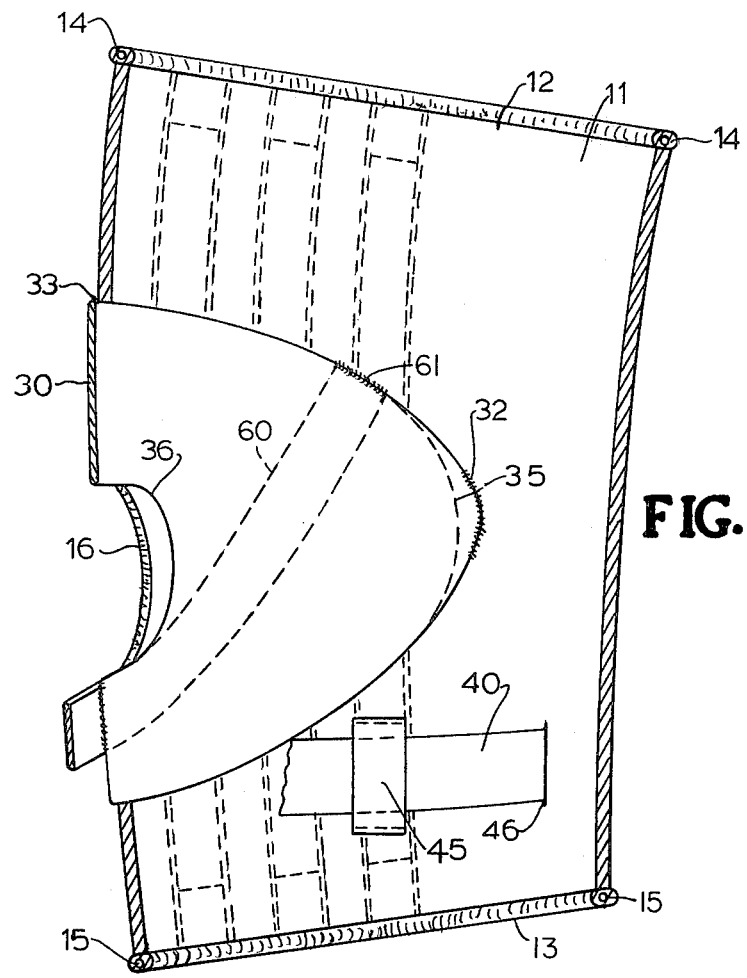
FIG. 5 is a slightly enlarged section view taken substantially along line 5—5 of FIG. 2.
Figure 6:
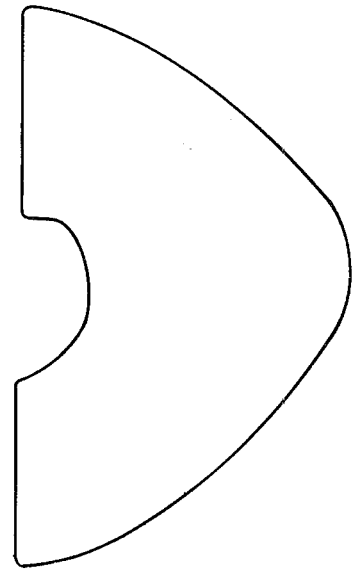
FIG. 6 is a plan view illustrating the semi-annular shape of one of the pads.

Referring to the drawings, a knee protector/stabilizer or brace 10 constructed in accordance with the present invention comprises a tubular, circular rib knit, seamless, elastic sleeve 11 which is highly stretchable in radial directions, indicated by arrows R—R, but not longitudinally, as indicated by arrows L—L. The sleeve is formed with the character of being a relatively thick compression bandage and is sized to have an unstretched diameter somewhat less than the wearer's leg so that the material is stretched as it is pulled over the knee into position. This holds the protector/stabilizer in place and also imparts some support to the knee region. The upper end 12 and lower end 13 terminate in sewn edges containing elastic bands 14, 15 respectively as illustrated in FIG. 5. Sleeve 11 in use conforms to the shape of the user's leg as shown in FIG. 1. A front opening 16 is located so as to generally surround and accommodate to the kneecap of the user and prevent binding of the material against the flexing kneecap as the user's leg is bent as in FIG. 1. Opening 16 is sewn along its edges and formed with an elastic material to allow stretching of the opening in use.

Longitudinally of sleeve 11 and adjacent each side of front opening 16 a plurality of vertical spiral stays 20 are attached to sleeve 11 by means of cloth strips 21 which fit over stays 20 and are sewn to sleeve 11 by stitching 22. Spiral stays as such are known in the art and in the present invention, there are three such stays on either side of opening 16 although there could be more or less depending upon the desired stiffness of knee protector/stabilizer 10. Stays 20 extend vertically or longitudinally of sleeve 11 and are parallel to each other as illustrated.

Figure 4:
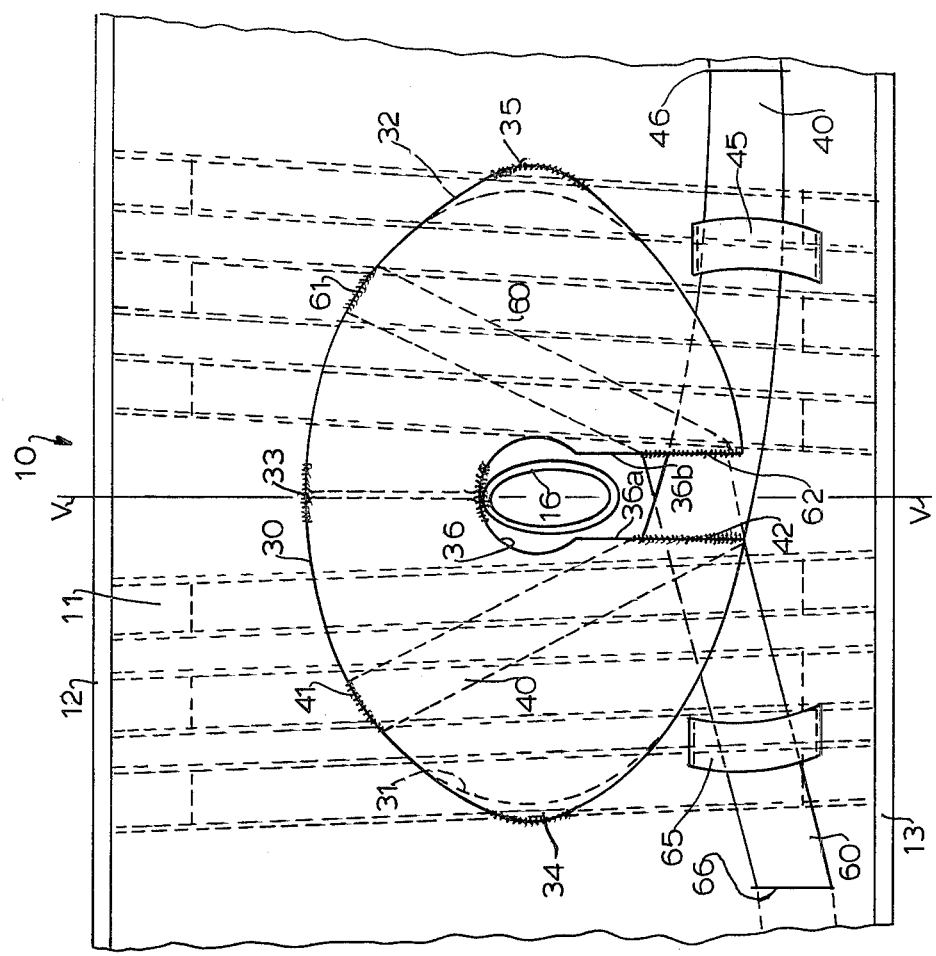
FIG. 4 is an inside plan view of the pad and strap arrangement with the protector/stabilizer or brace of the invention assumed to have been split so that it will lay flat for purposes of illustration.
Figure 3:
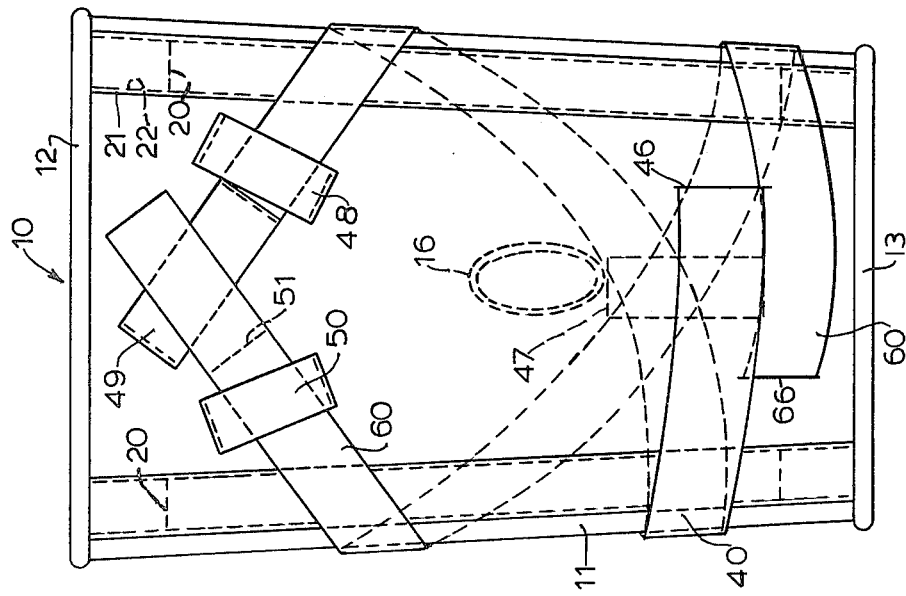
FIG. 3 is a rear view of the protector/stabilizer of FIG. 2.

On the inside of knee protector/stabilizer 10, a fabric covering 30, best seen in FIGS. 4 and 5, forms a pair of interconnected fabric pouches on opposite sides of central axis V—V (FIG. 4) and having sewn edges in which a pair of semi-annular shaped pads 31, 32 are loosely enclosed. Pads 31, 32 are preferably formed of relatively thick, e.g., ⅜", foam rubber material such as used in kneeling pads, or the like, and which offer substantial resistance to compression. Covering 30 is stitched to secure covering 30 to the inside wall of sleeve 11 at upper point 33 and outer side points 34 and 35 and is formed with a keyhole-shaped opening 36, the upper portion of which is preferably larger than opening 16. Opening 36 surrounds opening 16 within the brace. Spaced apart, sewn pad pocket edges 36a, 36b define the lower keyhole-shaped boundaries of opening 36.

An important aspect of the invention resides in the manner in which a pair of securing straps 40, 60 are employed for adjusting the positioning of pads 31, 32. In this regard, it will be noted that securing strap 40 has an inner end portion which is sewn to the unsecured upper edge of covering 30 by stitching 41 adjacent the inside wall of sleeve 11. This inner end portion of strap 40 extends downward behind covering 30 adjacent the inside wall of sleeve 11 to the lower unsecured edge of cover 30 where it is again stitched to covering 30 by stitching 42 on edge 36a. Strap 40 then crosses strap 60 and extends across and loosely through loop 45 sewn to the inside of sleeve 11 and then passes through a slit or opening 46 in the wall of sleeve 11. Outside sleeve 11, strap 40 spirals upwardly around the exterior of sleeve 11 and passes loosely through another loop 47 sewn to the exterior of sleeve 11 immediately below opening 16 and in which strap 40 again crosses strap 60. From loop 47, strap 40 passes loosely through another loop 48 which is sewn to sleeve 11 and terminates past loop 48 on the back side of sleeve 11 with a free end. It is highly desirable that the respective free ends of securing straps 40, 60 be releasably attachable to each other so as to be able to secure securing straps 40, 60 on the outside of sleeve 11 in desired relatively loose or relatively tight positions and thereby maintain pads 31, 32 in desired positions. For this purpose, the free end of strap 40 has on its outside surface sewn thereto a portion of a hook-loop-type Velcro fastener 49.

The inner end portion of the second securing strap 60 is sewn within sleeve 11 to an upper unsecured edge of covering 30 by stitching 61 peripherally spaced on covering 30 from stitching 41. The inner end portion of strap 60 then extends downward between covering 30 and the inside wall of sleeve 11 to a lower unsecured edge of cover 30 where it is stitched to cover 30 by stitching 62 on edge 36b. Strap 60 then crosses strap 40, passes loosely through loop 65 sewn to the inside of sleeve 11 and then passes through slit or opening 66 in the wall of sleeve 11.

The outer end portion of strap 60 then spirals upwardly, passes around the exterior of sleeve 11, passes loosely through loop 47 and extends upward so as to pass loosely through loop 50 and terminates with a free end on the back side of sleeve 11 and crossing strap 40. This free end of strap 60 has on its inside surface sewn thereto a portion of a mating hook-loop-type Velcro fastener 51 which mates with portion 49 on strap 40. Other types of releasable fasteners may of course be employed.

While not shown in detail, brace 10 of the invention may, if desired, be formed immediately below upper end 12 with a peripheral narrow band of elastic fabric of different lateral or radial stretch character than in the elastic body fabric forming sleeve 11. Also, in the area of sleeve 11, normally positioned behind the knee, the fabric may be formed with a greater lateral or radial stretch than in the fabric in front of the knee.

The brace or knee protector/stabilizer 10 by design fits snugly on the leg of the user but by pulling on straps 40, 60 an even greater degree of tighting may be achieved when fasteners 49, 51 are mated into a locking relationship. Pads 31, 32 are thus provided with some adjustability and which adjustability may be accomplished externally by pulling on or releasing straps 40, 60 respectively. Once knee protector/stabilizer 10 is in place on the user's leg, it is often desirable to slightly adjust the position of either pad 31 or pad 32 or possibly both pads. Heretofore, in prior art braces it would have been necessary to reach inside of sleeve 11 and attempt to position the pads and then withdraw the hand and repeat the process until the pads were properly positioned. However, with the present knee protector/stabilizer, such adjustment utilizing cover 30 and pads 31, 32 of the invention can be made externally utilizing straps 40, 60 and achieved quickly by the user without slowing down his activity.

What is claimed is:

1. A knee brace adapted for protecting and stabilizing the knee joint area of the user, comprising:
   (a) a tubular elastic knit fabric sleeve adapted to receive the leg of a user and to be positioned over and to cover the knee joint area, said sleeve having on the front side thereof a first opening formed therein for positioning over the kneecap of the leg and below said first opening, second and third peripherally-spaced openings adapted for passing securing straps therethrough;
   (b) internal pad means, comprising:
      (i) a pair of laterally-spaced, semi-annularly-shaped resilient pad members;
      (ii) a fabric cover providing on either side of a central vertical axis a pair of outwardly extending semi-annular-shaped pouches stitched to the inside of said sleeve on the outer sides thereof and conforming in shape to the shape of said pads and loosely enclosing said pads, said pouches having interconnecting fabric at the top of said cover secured to said sleeve and being separated and laterally-spaced in the bottom portion of said cover, whereby to provide a pair of opposed semi-annular-shaped fabric covered pads within said sleeve and around said opening and arranged such that the tops of said pads can remain relatively fixed while the bottoms of said pads are adjusted to conform the positioning of said pads to the shape of the knee joint area surrounding said kneecap; and
   (c) a pair of securing straps having inner end portions residing within and outer end portions residing outside said sleeve, said inner end portions being arranged so as to cross within said sleeve below said opening and so as to have each respective terminal end thereof secured to upper and lower edges of a respective said pouch adjacent the inner wall of said sleeve, said inner end portions extending outwardly through respective said peripherally-spaced second and third openings in said sleeve with said outer end portions forming continuations thereof and being arranged to spiral upwardly around said sleeve, to cross on the outside of said sleeve below said opening on the front of said sleeve and to terminate with free ends near the upper edge of said sleeve and on the back of said sleeve, said free ends having means associated therewith for enabling said free ends to be releasably secured together whereby said straps by loosening and tightening the same outside said sleeve may be employed to adjust the relative positioning and compression of said pads against the areas of the said knee joint which they contact.

2. A knee brace as claimed in claim 1 including a first loop secured outside and on the front of said sleeve below said first opening to maintain the crossing of said securing straps therein and second and third loops secured to the outside of said sleeve on the back side thereof to maintain the positioning of said free ends.

3. A knee brace adapted for protecting and stabilizing the knee joint area of the user, comprising:
   (a) a tubular elastic knit fabric sleeve adapted to receive the leg of a user and to be positioned over and to cover the knee joint area, said sleeve having on the front side thereof a first opening formed therein for positioning over the user's kneecap and below said first opening, second and third peripherally-spaced openings adapted for passing securing straps therethrough;
   (b) internal pad means, comprising:
      (i) a pair of laterally-spaced, resilient pad members shaped to conform to selected portions of said knee joint area to be compressed thereby; and
      (ii) first and second support means for supporting said pads separately and adjacent said first opening within said sleeve and arranged such that the tops of said pads can remain relatively fixed in position while the bottoms of said pads are adjusted laterally to conform the positioning of said pads to the shape of the knee joint area surrounding said kneecap; and (c) a pair of securing straps having inner end portions residing within and outer end portions residing outside said sleeve, said inner end portions being arranged so as to have each respective terminal end thereof secured to a respective said first or second pad support means adjacent the inner wall of said sleeve, said inner end portions extending from the terminal ends thereof outwardly through respective said peripherally-spaced second and third openings in said sleeve with said outer end portions forming continuations thereof and being arranged to extend and to terminate with free ends outside said sleeve, said free ends having means associated therewith for enabling said free ends to be releasably secured together whereby said straps by loosening and tightening the same outside said sleeve may be employed to adjust the relative positioning and compression of said pads within said sleeve against the areas of the said knee joint which they contact.

4. A knee brace adapted for protecting and stabilizing the knee joint area of the user, comprising:
(a) a tubular elastic knit fabric sleeve adapted to receive a leg of the user and to be positioned over and to cover the knee joint area, said sleeve having on the front side thereof a first opening formed therein for positioning over the user's kneecap and below said first opening, second and third peripherally-spaced openings adapted for passing straps therethrough;
(b) internal pad means, comprising:
 (i) resilient pad means shaped to conform to said knee joint area; and
 (ii) means for supporting said pad means adjacent said first opening within said sleeve and arranged such that the upper portion of said pad means can remain relatively fixed in position while the lower portion of said pad means can be adjusted laterally to conform the positioning of said pad means to the shape of the knee joint area surrounding said kneecap;
(c) a pair of straps having inner end portions residing within and outer end portions residing outside said sleeve, each said inner end portion being secured at the respective terminal end thereof to the lower portion of a respective said pad means, said inner end portions extending from the secured terminal ends thereof outwardly through respective said peripherally-spaced second and third openings in said sleeve with said outer end portions forming continuations thereof and being arranged to extend and to terminate with free ends outside said sleeve; and
(d) releasable securing means operatively associated with said strap free ends adapting said free ends to be releasably secured together whereby said straps by loosening and tightening the same outside said sleeve may be employed to adjust the relative positioning of said pad means within said sleeve against the area of the said knee joint.

* * * * *